United States Patent
Tets et al.

(10) Patent No.: US 10,266,869 B2
(45) Date of Patent: Apr. 23, 2019

(54) DEVICE FOR DETERMINING THE SENSITIVITY OF MICROORGANISMS TO ANTIMICROBIAL DRUGS

(71) Applicants: Viktor Veniaminovich Tets, St. Petersburg (RU); Georgy Viktorovich Tets, St. Petersburg (RU)

(72) Inventors: Viktor Veniaminovich Tets, St. Petersburg (RU); Georgy Viktorovich Tets, St. Petersburg (RU)

(73) Assignees: Viktor Veniaminovich Tets, Saint-Petersburg (RU); Georgy Viktorovich Tets, Saint-Petersburg (RU)

( * ) Notice: Subject to any disclaimer, the term of this patent is extended or adjusted under 35 U.S.C. 154(b) by 313 days.

(21) Appl. No.: 15/039,966

(22) PCT Filed: Oct. 27, 2014

(86) PCT No.: PCT/RU2014/000810
§ 371 (c)(1),
(2) Date: May 27, 2016

(87) PCT Pub. No.: WO2015/080622
PCT Pub. Date: Jun. 4, 2015

(65) Prior Publication Data
US 2016/0369319 A1    Dec. 22, 2016

(30) Foreign Application Priority Data
Nov. 28, 2013    (RU) .................................. 2013147669

(51) Int. Cl.
*C12Q 1/18* (2006.01)
*C12M 1/32* (2006.01)
*C12M 1/34* (2006.01)

(52) U.S. Cl.
CPC .............. *C12Q 1/18* (2013.01); *C12M 23/12* (2013.01); *C12M 41/34* (2013.01)

(58) Field of Classification Search
CPC .......... C12Q 1/18; C12Q 1/686; C12M 23/12; C12M 41/34; B01L 7/525; B01L 7/52;
(Continued)

(56) References Cited

U.S. PATENT DOCUMENTS 2,533,088 A * 12/1950 Brewer ................. C12M 23/10
                                                                  312/31.01
5,789,173 A    8/1998 Peck et al.
(Continued)

FOREIGN PATENT DOCUMENTS

BY         7596 U      10/2011
CN      203904353  *    5/2014 .............. C12M 1/34
(Continued)

OTHER PUBLICATIONS

Machine Translatin of CN 203904353 (Year: 2018).*
(Continued)

*Primary Examiner* — Michael L Hobbs
(74) *Attorney, Agent, or Firm* — Troutman Sanders LLP

(57) ABSTRACT

The invention relates to the field of microbiology. A device for determining the sensitivity of microorganisms to antimicrobial drugs is configured in the form of a sterile plate made from a plastic material with indentations and is provided with a hermetically sealing element which covers the sterile plate. The indentations are filled with a solid culture medium containing agar. In different indentations, the culture medium contains antimicrobial drugs or combinations thereof or serves as a control. Between the plate and the hermetically sealing element, the device contains a moisture-absorbing material with a rigid mesh situated ther-
(Continued)

ebelow. The device is provided with a transparent protective lid made from a rigid durable plastic.

7 Claims, 2 Drawing Sheets

(58) Field of Classification Search
CPC ........... B01L 2200/10; B01L 2200/143; B01L 2300/0627; B01L 2300/1811; B01L 2300/0829; B01L 2300/18; B01L 2300/0654; B01L 2300/1877; B01L 2300/1827; B01L 2300/1822; B01L 2400/0487; B01L 3/50273; B01L 3/502715; G01N 21/71; G01N 35/08; G06T 7/0012; G06T 7/11; G06T 2207/30072; G06T 2207/10004; Y10T 436/115831; Y10T 436/117497
See application file for complete search history.

(56) References Cited

U.S. PATENT DOCUMENTS

| | | | |
|---|---|---|---|
| 6,153,400 A | 11/2000 | Matsumura et al. | |
| 6,280,946 B2 | 8/2001 | Hyldig-Nielsen et al. | |
| 6,984,499 B2 | 1/2006 | Chen et al. | |
| 7,262,021 B1 | 8/2007 | Taintor | |
| 8,753,875 B2 | 6/2014 | Frimodt-Moller | |
| 8,900,856 B2 * | 12/2014 | Muller-Cohn ........... | A01N 1/00 435/287.1 |
| 2002/0076742 A1 | 6/2002 | Chen et al. | |
| 2004/0018585 A1 * | 1/2004 | Crouteau ............... | B01L 3/5085 435/34 |
| 2005/0276728 A1 * | 12/2005 | Muller-Cohn ........... | A01N 1/00 422/400 |
| 2006/0099567 A1 * | 5/2006 | Muller-Cohn ......... | A01H 4/001 435/1.1 |
| 2008/0307117 A1 * | 12/2008 | Muller-Cohn ........... | A01N 1/00 710/6 |
| 2008/0318268 A1 | 12/2008 | Olson et al. | |
| 2009/0068696 A1 | 3/2009 | Frimodt-Moller | |
| 2009/0291427 A1 * | 11/2009 | Muller-Cohn ......... | A01H 4/001 435/2 |
| 2009/0298132 A1 * | 12/2009 | Muller-Cohn ......... | A01H 4/001 435/91.51 |
| 2009/0310839 A1 | 12/2009 | Katzenelson et al. | |
| 2011/0269130 A1 | 11/2011 | Shi et al. | |
| 2011/0318814 A1 * | 12/2011 | Kshirsagar ............. | C12M 47/04 435/239 |
| 2012/0329675 A1 | 12/2012 | Olson et al. | |
| 2014/0170671 A1 * | 6/2014 | McGarr ................ | B01L 3/5025 435/7.1 |
| 2015/0284764 A1 | 10/2015 | Tets et al. | |

FOREIGN PATENT DOCUMENTS

| | | |
|---|---|---|
| JP | H1066598 A | 3/1998 |
| RU | 2061032 C1 | 5/1996 |
| RU | 2231554 C2 | 6/2004 |
| RU | 2262533 C2 | 10/2005 |
| RU | 2006111133 A | 10/2007 |
| RU | 69066 U1 | 12/2007 |
| RU | 2319746 C2 | 3/2008 |
| RU | 127749 U1 | 1/2012 |
| RU | 2505813 C1 | 1/2014 |
| WO | 1996/028570 A1 | 9/1996 |
| WO | 1999/018232 A1 | 4/1999 |
| WO | 2004050675 A1 | 6/2004 |
| WO | 2009/026920 A1 | 3/2009 |
| WO | 2011009213 A1 | 1/2011 |
| WO | 2014/074012 A1 | 5/2014 |

OTHER PUBLICATIONS

European Extended Search Report Issued in EP14866121.8, dated Apr. 28, 2017, 9 pages.
Ghannoum, Mahmoud A. et al, "Characterization of the Oral Fungal Microbiome (Mycobiome) in Healthy Individuals", PLOS (2010), vol. 6, Issue 1, e1000713, 8 pages.
US Food and Drug Administration "Chapter 3: types of Devices and predictive device" In: "Guidance for Industry and for FDA Reviewers Guidance on Review Criteria for Assessment of Antitiicrobial Susceptibility Devices" (1991), US Department of Health and Human Services, Washington DC USA, XP055364834, pp. 1-22.
Epstein S.S., "General model of microbial uncultivability in uncultivated microorganisms", Series: Microbiology Monographs, Springer, (2009), p. 131-150.
European Communication Pursuant to Rules 70(2) and 70a(2) EPC, Extended/Supplementary European Search Report Issued in EP13853343.5. dated Jun. 23, 2016, 7 pages.
International Search Report and Written Opinion Issued in PCT/RU2013/000394 dated Dec. 12, 2013, 11 pages and English Translation Thereof.
Isenberg H.D. Essential Procedures for Clinical Microbiology, ASM-PRESS (1998), pp. 208-215, 216-223, and 235-240.
Birger M.O., Spravochnik po mikrobiologicheskim i virusologicheskim metodam issledovaniya, Moskva, Medicina, 1973, pp. 177-178 and English Translation thereof.
International Preliminary Report on Patentability Issued in PCT/RU2013/000394 dated May 12, 2015, 4 pages and English Translation Thereof.
Lagace-Weins, P.R.S. et al., "Treatment of lower urinary tract infection caused by multidrug-resistant extended-spectrum-β-lactamase-producing *Escherichia coli* with amoxicillin/clavulanate: case report and characterization of the isolate" Journal of Antimicrobial Chemotherapy (2006), 57(6):1262-1263.
Lewis K. et al. "Persisters, biofilms, and the problem of culturability in incultivated microorganisms", Series: Microbiology Monographs, Springer, 2009. p. 181-194.
International Preliminary Report on Patentability Issued in PCT/RU2014/000810, dated May 31, 2016, 5 pages.
Zhou; Xia et al., "The vaginal bacterial communities of Japanese women resemble those of women in other racial groups" FEMS Immunology & Medical Microbiology (2010), vol. 58, p. 169-181.
Blood Agar, Thermofisher 2008, accessed at: https://tools.thermofisher.com/content/sfs/manuals/IFU1200.pdf.
Communication issued by the United States Patent and Trademark Office in U.S. Appl. No. 14/439,717, dated Sep. 12, 2017.
Dong, Q. et al., "The Microbial Communities in Male First Catch Urine are Highly Similar to Those in Paired Urethral Swab Specimens" (2011) PLoS One vol. 6, Issue 5, e19709, pp. 1-5.
Ellner, P.D. et al., "A New Culture Medium for Medical Bacteriology" The American Journal of Clinical Pathology (1966) vol. 45, No. 4, pp. 502-504.
European Communication issued by the European Patent Office in European Patent Application No. 13853343.5, dated Nov. 13, 2017, 5 pages total.
International Preliminary Report on Patentability and Written Opinion (including translation) issued by the International Searching Authority in International Patent Application No. PCT/RU2016/000383, dated Dec. 26, 2017, 9 pages total.
International Search Report (including translation) issued by the International Searching Authority in International Patent Application No. PCT/RU2016/000383, dated Oct. 20, 2016, 3 pages total.
Korotchenko, H.M. et al., "Izuchenie Ustoichivosti Violuratnykh Kompleksov Nekotorykh D-i F-metallov" Zhurnal Neorganicheskoi Khimii (2012) vol. 57, No. 1, pp. 141-147.
Oliver, J.D., "Recent Findings on the Viable but Nonculturable State in Pathogenic Bacteria" (2010) FEMS Microbiology Reviews (2010) vol. 34, pp. 415-425.
Petrosino, J.F. et al., "Metagenomic Pyrosequencing and Microbial Identification" Clinical Chemistry (2009) vol. 55, No. 5, pp. 856-866.
Poliak, M.C. et al., "Pitatelnye Sredy Dlia Meditsinskoi Mikrobiologii" St. Petersburg (2002), 80 pages total.

(56) References Cited

OTHER PUBLICATIONS

By 7596 U (Uchrezhdenie Obrazovanya, Vitebsky Gosudartsvenny Ordena Druzhby Narodov Meditainsky Universitet, (Oct. 30, 2011), p. 2.

International Search Report and Written Opinion Issued in PCT/RU2014/000810, dated Jan. 15, 2015, 8 pages.

Opredefenie chuvstviteinosti mikrporganizmov k antinakterialnyrn preparatam, metodicheskie rekomendatsii. Klinicheskaya Mikrobiologiya Antimikrobnaya Khimioterapiya (2004), vol. 06:04. p. 311-312.

Communication issued by the United States Patent and Trademark Office in U.S. Appl. No. 14/439,717, dated Mar. 15, 2018.

European Communication Pursuant to Article 94(3) EPC issued by the European Patent Office in European Application No. 13 853 343.5, dated May 24, 2018, 5 pages total.

Funk, D.J. et al., "Antimicrobial Therapy for Life-Threatening Infections: Speed is Life" Critical Care Clinics (2011) vol. 27 pp. 53-76.

Hellenkamp, K. et al., "Early Pneumonia and Timing of Antibiotic Therapy in Patients After Nontraumatic Out-of-Hospital Cardiac Arrest" Critical Care (2016) vol. 20, No. 31, 10 pages total.

\* cited by examiner

US 10,266,869 B2

DEVICE FOR DETERMINING THE SENSITIVITY OF MICROORGANISMS TO ANTIMICROBIAL DRUGS

CROSS-REFERENCE TO RELATED APPLICATIONS

This application is a U.S. National Phase of International Patent Application No. PCT/RU2014/000810, filed Oct. 27, 2014, which claims priority to Russian Patent Application No. 2013147669, filed Nov. 28, 2013, all of which applications are herein incorporated by reference in their entirety.

TECHNICAL FIELD

The invention relates to the field of microbiology and in particular—to devices used for seeding of microorganisms in order to determine their sensitivity to antimicrobial drugs.

BACKGROUND

The most common and simple device for determining the sensitivity of microorganisms to antimicrobial drugs is the Petri dish, RU 69066 U1.

The Petri dish is a small-size shallow cylindrical vessel made from plastic, glass or ceramics. However, in determining the sensitivity of microorganisms to various antimicrobial drugs one has to use a rather large number of Petri dishes corresponding to the number of the drugs, which creates inconvenience and overloads the desktop.

Petri dish RU 127749 U1 containing an insert in the form of a cone, divided into two or more through sectors by vertical partitions, is known from the prior art. The device is designed for comparative evaluation of nutrient media in bacteriological diagnosis. Different by composition nutrient media are poured into the insertion sectors. The microorganism being tested is seeded into each of the media. The device can also be used for determining the sensitivity of microorganisms to antimicrobial drugs. In this case, the same medium is used, but different antimicrobial drugs are put into the insertion sectors.

The disadvantage of this technical solution is the limited ability to divide the insert into sectors, as the increase in their number (practically, over three) leads either to an unacceptably small volume of each sector, or to a significant increase in the diameter of the Petri dish.

The device for determining the sensitivity of microorganisms to antimicrobial drugs configured in the form of a sterile plate made from a plastic material. The board has recesses for introduction of the nutrient medium, the antimicrobial agent and the microorganism being tested for sensitivity to these substances in the laboratory conditions therein. From the top side, the sterile board is closed by a sealing element, US 2008/0318268 A1.

This technical solution is taken as a prototype of the present invention.

In the original (factory) state, the indentations in the board are empty. After removing the protective film in the laboratory, a medium and the antimicrobial agents are put in them, and the microorganisms are seeded. Their sensitivity to a particular drug is determined on the basis of the degree of microbiological growth.

The disadvantage of this technical solution is the fact that its use is associated with a considerable time consumption and inconvenience in the laboratory conditions, associated with the placement of the nutrient medium in the indentations and putting of various antimicrobial drugs into various indentations with the medium at the site where the works to determine the susceptibility of microorganisms to antimicrobial drugs are executed.

SUMMARY

It is an object of the present invention to provide a sterile plate for determining the sensitivity of microorganisms to antimicrobial drugs that ensures reduction of the time consumption for this work, and improves the usability in vitro.

According to the invention, in the device for determining the sensitivity of microorganisms to antimicrobial drugs configured in the form of a sterile plate made from plastic material with indentations provided with a sealing element that covers it, the indentations are filled with a solid culture medium containing agar; at that, in different indentations, the culture medium contains antimicrobial drugs or combinations thereof or serves as a control; between the plate and the hermetically sealing element, the device contains a moisture-absorbing material with a rigid mesh situated therebelow; the device is equipped with a transparent protective lid made of a rigid durable plastic; the means for retention of the solid culture medium in the indentations may be configured in the form of broadenings in the bottom of the indentations; the means for retention of the solid culture medium may be configured in the form of cantilever protrusions on sidewalls of the indentations; the covering sealing element may be configured in the form of a film made of a plastic material; the sterile plate may be provided with stiffening ribs; additional indentations may be made in the plate.

The applicant has not found any technical solutions identical to the present invention, which enables to conclude that the invention conforms to the criterion "Novelty" (N).

BRIEF DESCRIPTION OF DRAWINGS

The invention is further explained by way of a detailed description of examples of its embodiment, with reference to drawings, which show.

DETAILED DESCRIPTION

Figure 1:
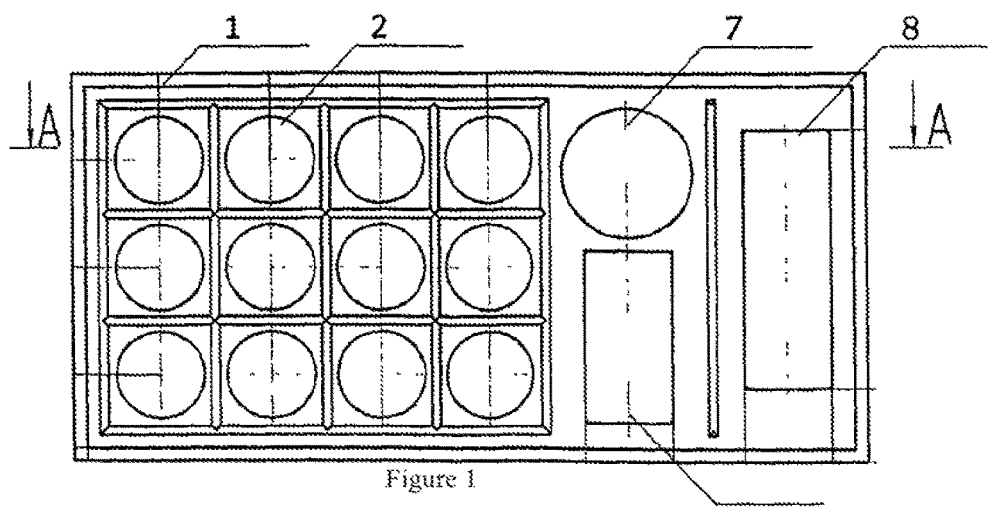
FIG. 1—Illustrates a top view of a sterile plate of an example of the present invention.
Figure 2:
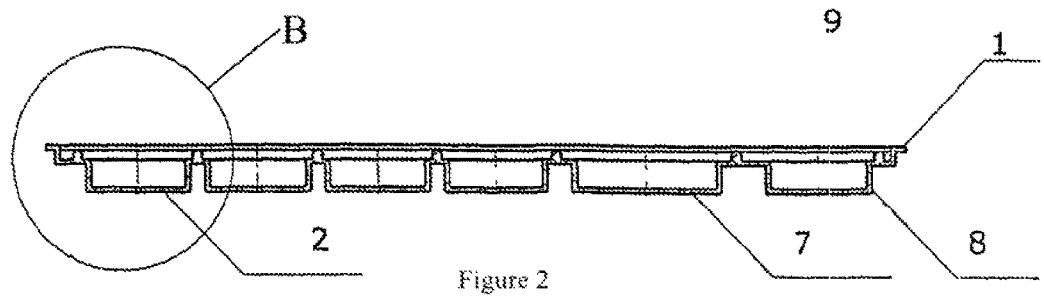
FIG. 2—Illustrates a cross-section AA in FIG. 1.
Figure 3:
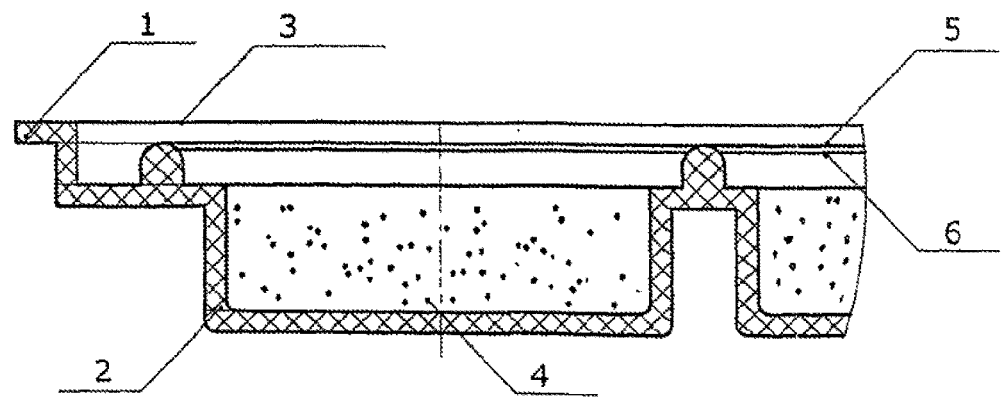
FIG. 3 Illustrates section B in FIG. 2 on an enlarged scale.
Figure 4:
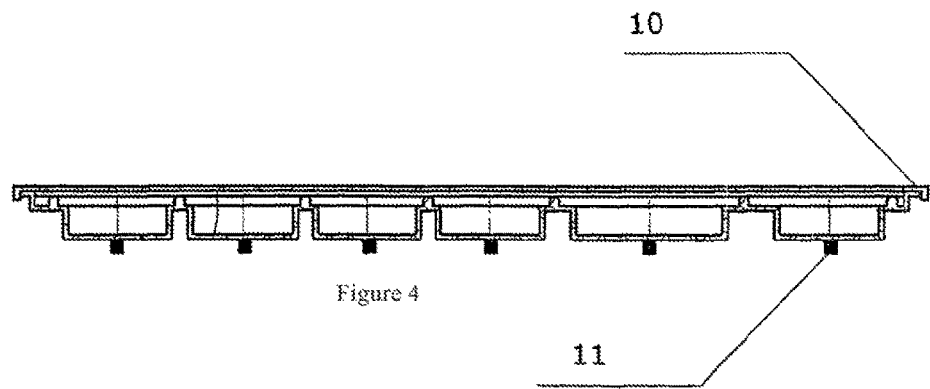
FIG. 4 Illustrates another example of a cross-section with a protective cap and reinforcement ribs.

The device for determining the sensitivity of microorganisms to antimicrobial drugs is configured in the form of a sterile plate made from a plastic material. The plate 1 has indentations 2, in the particular example there are 12 indentations 2, the diameter of each indentation is 2-20 mm. The sterile plate 1 is provided with a hermetically sealing element 3, in particular—a thin film of plastic material brazed to plate 1 along its contour. All indentations 2 are filled with a solid culture medium 4 containing agar at the manufacturing plant; due to its physical properties and the adhesive properties of the plate 1 material, the medium is sufficiently and securely fixed in the indentations 2 and together with the plate 1 forms a single structure; at that, in different indentations, the culture medium contains antimicrobial drugs or combinations thereof or serves as a control.

Figure 5:
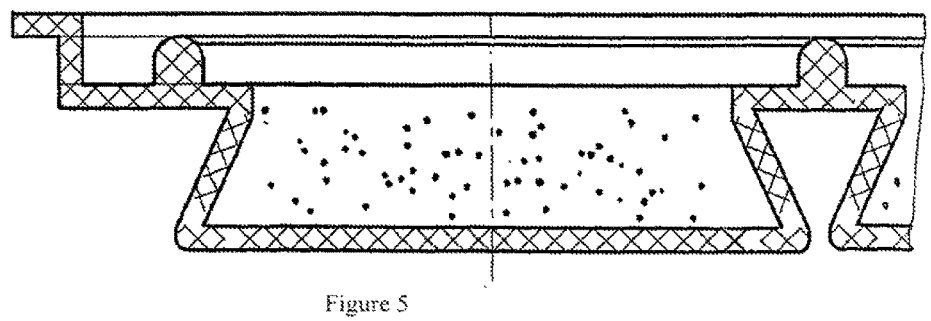
FIG. 5 Illustrates yet another example with indentations in the plate.
Figure 6:
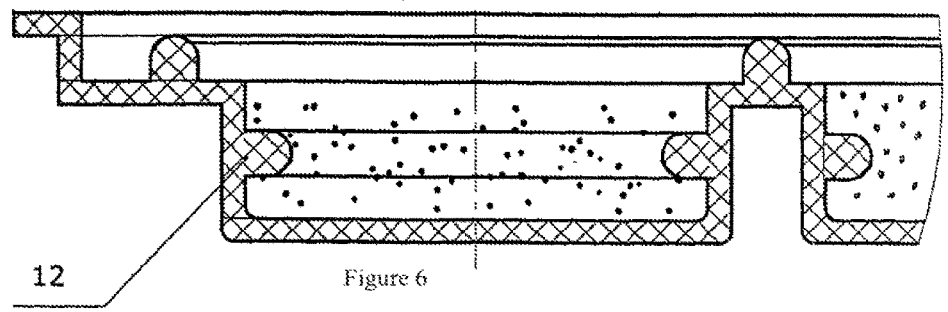
FIG. 6 Illustrates a further example of indentations in the plate.

To improve the reliability of coupling of the solid culture medium 4 with the surface of the indentations 2 the means for retention of the solid culture medium in the indentations 2 may be configured in the form of broadenings in the bottom of the indentations 2 (FIG. 5) or in the form of cantilever protrusions 12 located on sidewalls of the indentations 2 (FIG. 6).

The solid culture medium in various indentations 2, in this example, in ten indentations contains various antimicrobial drugs—antibacterial and/or antifungal antibiotics and/or antiseptics. In two of the indentations 2 the medium 4 is a control one, i.e., does not contain any antimicrobial drugs. Between the plate 1 and the hermetically sealing element 3 the moisture-absorbing material 5 is placed, in particular—filter paper. This material absorbs moisture vapor arising after pouring of the melted medium 4 into indentations 2 in the factory conditions, wherein the medium 4 has a temperature of about 60° C.

Under the moisture-absorbing material 5 the rigid mesh 6 is placed, which is made of plastic and prevents its sagging when wet. After manufacturing of the device, the material 5, which has absorbed moisture, provides the required humidity conditions in the indentations 2 filled with the solid culture medium 4.

The plate 1 also has additional indentations 7, 8, 9, whereby the indentation 7 can be used for breeding of a pathological material, and indentations 8 and 9 are support ones and can be used to accommodate, for example, material stirring rods etc. during introduction of the pathologic material into the culture medium.

The device is provided with a protective cover 10 made of a rigid durable plastic (transparent in the particular example) preventing damage to the hermetically sealing element 3. To improve the mechanical strength and rigidity, the sterile plate 1 is provided with reinforcement ribs 11.

The device is manufactured in the factory conditions and delivered to the laboratory assembled, where the process of determination of sensitivity of the microorganisms contained in the pathological material to various most widely used antimicrobial drugs. In the laboratory, the protective cover 10 is removed and the hermetically sealing element 3 (the film) is separated from the plate 1. Since the solid culture medium 4 with various antimicrobial drugs is placed and firmly fixed in the indentations 2 at the factory, the only operation carried out in the laboratory is the introduction of the beforehand diluted pathological material comprising the tested microorganisms into the culture medium 4 located in the indentations 2 (including those containing the culture medium). Then the plate 1 is placed into an incubator. After a certain period (4-120 hours), the indentations 2, in which there is a significant growth of microorganisms are determined, and compare with the condition of the microorganisms in the indentations 2 containing the control medium (without antimicrobial drugs). The presence of an antimicrobial drug is indicated on plate 1 at the plant manufacturing the device next to the respective indentation 2 or on the transparent protection lid 10. Thus, by consideration of the extent of microbial growth (or lack of growth) the conclusion on the sensitivity of a microorganism to a particular antimicrobial formulation is made.

The implementation of this invention ensures a technical result consisting in a significant reduction of time consumption and improving the ease of use in the laboratory conditions.

The device can be manufactured by means of common constructional materials and factory equipment. The prototype samples of the device were successfully tested in the laboratory of the Department of Microbiology, Virology and Immunology of the 1st St. Petersburg Medical University, which allows to make the conclusion that this invention meets the "Industrial Applicability" ("IA") patentability criterion.

The invention claimed is:

1. A device for determining the sensitivity of microorganisms to antimicrobial drugs, comprising:
a sterile plate made from plastic material;
a plurality of indentations formed in the sterile plate;
a hermetically sealing element sealing at least the plurality of indentations;
a moisture-absorbing material disposed between the plate and the hermetically sealing element;
a rigid mesh made of plastic is disposed under the moisture-absorbing material;
a transparent protective lid made of a rigid durable plastic is disposed over the sterile plate; and
a solid culture medium containing agar disposed in at least one of the plurality of indentations;
wherein the culture medium in different indentations contains at least one of an antimicrobial drug, combinations of antimicrobial drug, and a control.

2. The device of claim 1 wherein the plurality of indentations comprise a retention device retaining the solid culture medium in the plurality of indentations.

3. The device of claim 2 wherein the retention device comprises broadenings in the bottom of the indentations.

4. The device of claim 2 wherein the retention device comprises cantilever protrusions on sidewalls of the indentations.

5. The device of claim 1 wherein the hermetically sealing element comprises a film made of a plastic material.

6. The device of claim 1 wherein the sterile plate further comprises reinforcement ribs.

7. The device of claim 1 wherein the plurality of indentations comprise additional indentations.

* * * * *